(12) United States Patent
Yang et al.

(10) Patent No.: US 8,519,208 B2
(45) Date of Patent: Aug. 27, 2013

(54) PROCESSES FOR SYNTHESIZING ETHYLBENZENE FROM ETHANOL AND BENZENE

(75) Inventors: Weimin Yang, Shanghai (CN); Hongmin Sun, Shanghai (CN); Wenjie Liu, Shanghai (CN); Bin Zhang, Shanghai (CN); Zhenhao Shen, Shanghai (CN); Mingyao Huan, Shanghai (CN); Hongyu Zhang, Shanghai (CN)

(73) Assignees: China Petroleum & Chemical Corporation, Bejing (CN); Shanghai Research Institute of Petrochemical Technology, Sinopec, Shangai (CN)

( * ) Notice: Subject to any disclaimer, the term of this patent is extended or adjusted under 35 U.S.C. 154(b) by 255 days.

(21) Appl. No.: 13/158,709

(22) Filed: Jun. 13, 2011

(65) Prior Publication Data

US 2011/0306810 A1   Dec. 15, 2011

(30) Foreign Application Priority Data

Jun. 11, 2010 (CN) ............. 2010 1 0200020
Jun. 11, 2010 (CN) ............. 2010 1 0200039
Jun. 11, 2010 (CN) ............. 2010 1 0200049

(51) Int. Cl.
*C07C 2/66* (2006.01)
*C07C 6/12* (2006.01)

(52) U.S. Cl.
USPC .................. 585/323; 585/467; 585/475

(58) Field of Classification Search
USPC .................................. 585/323, 467, 475
See application file for complete search history.

(56) References Cited

U.S. PATENT DOCUMENTS 7,279,608 B2 * 10/2007 Ghosh et al. ............ 585/467

FOREIGN PATENT DOCUMENTS

| CN | 1201773 | 12/1998 |
|---|---|---|
| CN | 1187299 | 2/2005 |
| CN | 101121626 | 2/2008 |
| CN | 101168124 | 4/2008 |
| CN | 101565346 | 10/2009 |

* cited by examiner

*Primary Examiner* — Thuan D Dang
(74) *Attorney, Agent, or Firm* — Finnegan, Henderson, Farabow, Garrett & Dunner, LLP (57) ABSTRACT

Processes for catalytically synthesizing ethylbenzene from ethanol and benzene comprising:
1) reacting a first mixture comprising ethanol and benzene with at least one catalyst chosen from binder-containing alkylation catalysts and binder-free alkylation catalysts in an alkylation reactor to obtain a second mixture comprising residual benzene, ethylbenzene, diethylbenzene, and water;
2) passing the second mixture successively through a benzene recovery tower, an ethylbenzene recovery tower, and a polyethylbenzene recovery tower to obtain separated water, separated benzene, separated ethylbenzene, and separated diethylbenzene; and
3) reacting a third mixture with at least one transalkylation catalyst in a transalkylation reactor, wherein the third mixture comprises at least some of the separated benzene and at least some of the separated diethylbenzene at a weight ratio ranging from about 2:1 to about 10:1.

26 Claims, 1 Drawing Sheet

PROCESSES FOR SYNTHESIZING ETHYLBENZENE FROM ETHANOL AND BENZENE

This application claims priority under 35 U.S.C. §119 to Chinese Patent Application No. 201010200049.3, filed Jun. 11, 2010, Chinese Patent Application No. 201010200039.X, filed Jun. 11, 2010, and Chinese Patent Application No. 201010200020.5, filed Jun. 11, 2010.

The present disclosure relates to processes for synthesizing ethylbenzene from ethanol and benzene.

Styrene is an important raw material for preparation of various polymers such as polystyrene, ABS, AS, styrene butadiene rubber, and unsaturated polyesters. In addition, styrene is often used as an intermediate reactant in various organic reactions and is commonly used for production, for example, of drugs, coating materials, pigments, and textiles. Thus, there is a strong demand for styrene, particularly in, for example, the automobile, insulator, packaging, and daily chemical industries.

Styrene is most commonly produced by catalytic dehydrogenation of ethylbenzene. In fact, about 90% or more of ethylbenzene is used for production of styrene. Thus, the ever increasing demand for styrene produces a corresponding demand for more ethylbenzene.

Ethylbenzene can be obtained from an alkylation reaction between benzene and ethylene, usually in the presence of silicon-aluminum catalysts such as alumina or silica-alumina. The alkylation reaction of benzene and ethylene is generally conducted at a temperature ranging from about 350° C. to about 500° C., under a pressure ranging from about 0.5 MPaG to about 2 MPaG, and in a gas phase. The alkylation reaction of benzene and ethylene produces mainly ethylbenzene, but small amounts of light compounds such as propyl benzene, butyl benzene, diphenyl compounds, and impurities with high boiling points are also produced. See Chinese Patent Nos. ZL97106648.2, ZL02155114, and ZL97106448.2.

Ethylene, used for the production of ethylbenzene as mentioned above, can usually be produced from the thermo-cracking of naphtha originating from crude oil. The rise of prices for crude oil thus drives up the prices for ethylene. In addition, areas that have limited accesses to crude oil may not be able to produce enough ethylene. Accordingly, there is a need to find an alternative way of producing ethylene without the use of crude oil. And one way of achieving that goal is to produce ethylene through the dehydration of ethanol.

Due to the rapid development of biochemical engineering technology, the cost for obtaining ethanol has greatly decreased. For instance, ethanol can now be produced through fermentation of crops, such as maize and cassava, and crop straw. The falling cost of ethanol incentivized certain industries to synthesize ethylbenzene using ethylene produced from the dehydration of ethanol. See e.g., Chinese Patent Nos. ZL200810043303.6, ZL200610114032.X, and ZL200610029972.9. However, ethanol dehydration processes for the production of ethylene are energy intensive and can involve side reactions leading to low conversion of ethanol to ethylene. Those disadvantages have compromised the benefits of using the low-cost ethanol as a source material for producing ethylene as an intermediate for producing ethylbenzene.

Nonetheless, catalytic processes that use ethanol instead of ethylene for synthesizing ethylbenzene can have certain competitive advantages. The catalyst, however, should be capable of being regenerated for a long time and thus have a long lifetime. The catalyst for such processes should also have both high selectivity and capability of converting a substantial amount of ethanol to minimize the generation of impurities such as xylene.

Disclosed herein are processes for synthesizing ethylbenzene from ethanol and benzene. Some advantages associated with the use of the processes disclosed herein include, for example: using ethanol instead of ethylene as a starting material to synthesize ethylbenzene from benzene, and providing (1) low cost for the starting materials, (2) high ethanol conversion rate, (3) high ethanol selectivity, and/or (4) high catalytic stability.

Provided herein is a process for synthesizing ethylbenzene from ethanol and benzene, comprising:
1) reacting a first mixture comprising ethanol and benzene at a molar ratio ranging from about 2:1 to about 8:1 in a gas phase with at least one binder-containing alkylation catalyst in an alkylation reactor to produce a second mixture comprising benzene, ethylbenzene, diethylbenzene, and water;
2) passing the second mixture successively through a benzene recovery tower, an ethylbenzene recovery tower, and a polyethylbenzene recovery tower to obtain separated water, separated benzene, separated ethylbenzene, and separated diethylbenzene;
3) reacting a third mixture with at least one transalkylation catalyst in a transalkylation reactor to produce additional ethylbenzene, wherein the third mixture comprises at least some of the separated benzene and at least some of the separated diethylbenzene at a weight ratio ranging from about 2:1 to about 10:1, wherein the at least one binder-containing alkylation catalyst comprises the following components:
a) at least one ZSM-5 molecular sieve present in an amount ranging from about 40% to about 90% by weight relative to the total weight of the at least one binder-containing alkylation catalyst, wherein the at least one ZSM-5 molecular sieve comprises silica ($SiO_2$) and alumina ($Al_2O_3$) at a molar ratio ($SiO_2$:$Al_2O_3$) ranging from about 30:1 to about 400:1 and at least one crystalline particle with a diameter ranging from about 5 nm to about 350 nm;
b) at least one rare earth metal oxide present in an amount ranging from about 0.1% to about 10% by weight relative to the total weight of the at least one binder-containing alkylation catalyst; and
c) at least one binder chosen from alumina and silica present in an amount ranging from about 9% to about 59% by weight relative to the total weight of the at least one binder-containing alkylation catalyst.

In some embodiments, the total amount of the components (a), (b), and (c) in the at least one binder-containing alkylation catalyst equals to 100% by weight of the at least one binder-containing alkylation catalyst.

In some embodiments, the at least one binder-containing alkylation catalyst has been treated with steam and then phosphoric acid, dried, and calcinated, before it is used in an alkylation reaction disclosed herein. The conditions for treating the at least one alkylation catalyst with steam comprise, for example, treating the at least one alkylation catalyst with steam under an atmospheric pressure and at a temperature ranging from about 400° C. to about 800° C. for a period of time ranging from about 1 hour to about 20 hours. The conditions for treating the at least one alkylation catalyst with phosphoric acid comprise, for example, treating the at least one alkylation catalyst with a phosphoric acid solution at a concentration ranging from about 0.05 mol/l to about 15.0 mol/l and at a temperature ranging from about 5° C. to about 95° C. for a period of time ranging from about 1 hour to about 20 hours, wherein the weight ratio of the phosphoric acid solution to the at least one alkylation catalyst ranges from about 1:1 to about 20:1.

In some embodiments, the at least one ZSM-5 molecular sieve comprises at least one crystalline particle with a diameter ranging, for example, from about 10 nm to about 250 nm, such as from about 20 nm to about 200 nm. The crystalline particle diameter disclosed herein can be determined by Scan Electronic Microscope (SEM). The at least one ZSM-5 molecular sieve comprises silica ($SiO_2$) and alumina ($Al_2O_3$) at a molar ratio ($SiO_2$:$Al_2O_3$) ranging, for example, from about 50:1 to about 300:1.

In some embodiments, the at least one binder-containing alkylation catalyst comprises: at least one ZSM-5 molecular sieve in an amount ranging from about 55% to about 85% by weight relative to the total weight of the at least one binder-containing alkylation catalyst, at least one binder in an amount ranging from about 14% to about 44% by weight relative to the total weight of the at least one binder-containing alkylation catalyst, and at least one rare earth metal oxide in an amount ranging from about 0.1% to about 2.0% by weight relative to the total weight of the at least one binder-containing alkylation catalyst.

In some embodiments, the at least one rare earth metal oxide is chosen, for example, from lanthanum oxides, cerium oxides, and praseodymium oxides. In one embodiment, the at least one rare earth metal oxide is chosen from lanthanum oxides.

In some embodiments, the conditions for treating the at least one binder-containing alkylation catalyst with steam comprise, for example, treatment under atmospheric pressure and at a temperature ranging from about 480° C. to about 650° C. for a period of time ranging from about 2 hours to about 10 hours, such as from about 3 hours to about 10 hours.

In some embodiments, the conditions for treating the at least one binder-containing alkylation catalyst with phosphoric acid comprises, for example, treating the at least one alkylation catalyst with a phosphoric acid solution at a concentration ranging from about 0.1 mol/l to about 2.5 mol/l and at a temperature ranging from about 30° C. to about 95° C. for a period of time ranging from about 2 hours to about 16 hours, such as from about 3 hours to about 16 hours, the weight ratio of the phosphoric acid solution to the at least one alkylation catalyst ranging from about 2:1 to about 10:1.

In certain embodiments, the reaction in the alkylation reactor is conducted at a temperature ranging from about 320° C. to about 450° C., under a pressure ranging from about 0.5 MPa to about 2.0 MPa, at a weight hourly space velocity (weight of feed flowing per unit weight of the catalyst per hour) of ethanol ranging from about 0.6 $hour^{-1}$ to about 2.5 $hour^{-1}$, and with a molar ratio of benzene to ethanol ranging from about 4.0:1 to about 7.0:1.

In certain embodiments, the benzene recovery tower is operated under a pressure ranging from about 0.4 MPaG to about 2.0 MPaG, a temperature at the top of the tower ranging from about 125° C. to about 200° C., a temperature at the bottom of the tower ranging from about 200° C. to about 300° C., and with a reflux ratio ranging from about 0.8:1 to about 2:1.

In some embodiments, the ethylbenzene recovery tower is operated under a pressure ranging from about 0.0 MPaG to about 0.5 MPaG, a temperature at the top of the tower ranging from about 135° C. to about 200° C., a temperature at the bottom of the tower ranging from about 190° C. to about 250° C., and with a reflux ratio ranging from about 2:1 to about 6:1.

In some embodiments, the polyethylbenzene recovery tower is operated under a pressure ranging from about −0.1 MPaG to about 0.2 MPaG, a temperature at the top of the tower ranging from about 100° C. to about 220° C., a temperature at the bottom of the tower ranging from about 190° C. to about 250° C., and with a reflux ratio ranging from about 0.1:1 to about 2:1.

In some embodiments, the reaction in the transalkylation reactor (operation (3)) is carried out in a gas phase, the at least one transalkylation catalyst is chosen from ZSM-5 molecular sieve catalysts, and the transalkylation reactor is operated under the following conditions: a reaction temperature ranging from about 350° C. to about 460° C., a reaction pressure ranging from about 0.20 MPa to about 1.0 MPa, a total space velocity of from about 5 $hour^{-1}$ to about 40 $hour^{-1}$, and a weight ratio of benzene to polyethylbenzene ranging from about 3:1 to about 6:1.

In another embodiment, the reaction in the transalkylation reactor (operation (3)) is carried out in a liquid phase, the transalkylation catalyst is chosen from type β and type γ molecular sieve catalysts, and the transalkylation reactor is operated under the following conditions: a reaction temperature ranging from about 150° C. to about 280° C., a reaction pressure ranging from about 2.0 MPaG to about 3.5 MPaG, a weight hourly space velocity of liquid ranging from about 1.0 $hour^{-1}$ to about 3.0 $hour^{-1}$, and a weight ratio of benzene to polyethylbenzene ranging from about 3:1 to about 6:1.

In some embodiments, the at least one binder-containing alkylation catalyst comprising at least one binder is prepared by a process comprising:

i) Carrying out hydrochloric acid exchange, washing, baking, and calcinating the at least one ZSM-5 molecular sieve having a molar ratio of silica to alumina ($SiO_2$/$Al_2O_3$) ranging from about 30:1 to about 400:1 and at least one crystalline particle with a diameter ranging from about 5 nm to about 350 nm under conditions known to one of ordinary skill in the art, to obtain at least one HZSM-5 molecular sieve.

ii) Loading the at least one HZSM-5 molecular sieve with at least one rare earth metallic oxide: in one embodiment, impregnating the at least one HZSM-5 molecular sieve with a rare earth saline solution at a concentration ranging from about 0.002 mol/l to about 2.0 mol/l at a temperature ranging from about 10° C. to about 60° C. for a period of time ranging from about 1 hour to about 15 hours, the weight ratio of the rare earth saline solution to the at least one HZSM-5 molecular sieve ranging from about 0.5:1 to about 10:1; then baking, and calcinating, to obtain the at least one HZSM-5 molecular sieve comprising at least one rare earth oxide. In another embodiment, the rare earth saline solution is at a concentration ranging from about 0.05 mol/l to about 1.0 mol/l, the weight ratio of the rare earth saline solution to the at least one HZSM-5 molecular sieve ranges from about 1:1 to about 5:1, an impregnation temperature ranges from about 20° C. to about 40° C., and an impregnation duration ranges from about 2 hours to about 10 hours.

iii) Shaping the at least one binder-containing alkylation catalyst: in one embodiment, shaping the at least one HZSM-5 molecular sieve comprising the at least one rare earth obtained in operation (ii) together with at least one binder chosen from alumina and silica sols, extruding the at least one alkylation catalyst in the form of a strip with a diameter (φ) of 1.8 mm. That is followed by subjecting said catalyst to baking at about 110° C. for about 10 hours and calcinating at about 550° C. for about 4 hours.

iv) Treating with steam: the at least one alkylation catalyst is treated with steam at a temperature ranging from about 400° C. to about 800° C. for a period of time ranging from about 1 hour to about 20 hours so as to improve the hydrothermal stability of the catalyst.

v) Treating with phosphoric acid: after treating the at least one alkylation catalyst with steam, treating the at least one alkylation catalyst with a phosphoric acid solution at a concentration ranging from about 0.05 mol/l to about 15.0 mol/l at a temperature ranging from about 5° C. to about 95° C. for a period of time ranging from about 1 hour to about 20 hours, the weight ratio of the phosphoric acid solution to the catalyst ranging from about 1:1 to about 20:1.

vi) Drying and calcinating the at least one alkylation catalyst.

Also provided herein are processes for synthesizing ethylbenzene from ethanol and benzene, comprising:

1) reacting a first mixture comprising ethanol and benzene at a molar ratio ranging from about 2:1 to about 8:1 in a gas phase with at least one binder-free alkylation catalyst in an alkylation reactor to produce a second mixture comprising benzene, ethylbenzene, diethylbenzene, and water;

2) passing the second mixture successively through a benzene recovery tower, an ethylbenzene recovery tower, and a polyethylbenzene recovery tower to obtain separated water, separated benzene, separated ethylbenzene, and separated diethylbenzene;

3) reacting a third mixture with at least one transalkylation catalyst in a transalkylation reactor to produce additional ethylbenzene, wherein the third mixture comprises at least some of the separated benzene and at least some of the separated diethylbenzene at a weight ratio ranging from about 2:1 to about 10:1, wherein the at least one binder-free alkylation catalyst comprises the following components:

a) at least one binder-free ZSM-5 molecular sieve present in an amount ranging from about 90% to about 99.9% by weight relative to the total weight of the at least one binder-free alkylation catalyst, wherein the at least one binder-free ZSM-5 molecular sieve comprises silica ($SiO_2$) and alumina ($Al_2O_3$) at a molar ratio ($SiO_2$:$Al_2O_3$) ranging about 30:1 to about 400:1 and at least one crystalline particle with a diameter ranging from about 5 nm to about 350 nm; and b) at least one rare earth metal oxide present in an amount ranging from about 0.1 to about 10% by weight relative to the total weight of the at least one binder-free alkylation catalyst.

In some embodiments, the total amount of the components (a) and (b) in the at least one binder-free alkylation catalyst equals to 100% by weight of the at least one binder-free alkylation catalyst.

In some embodiments, the at least one binder-free alkylation catalyst is treated with steam and then phosphoric acid, dried, and calcinated, before it is used in an alkylation reaction. The conditions for treating the catalyst with steam comprise, for example, treating the catalyst with steam under atmospheric pressure at a temperature ranging from about 400° C. to about 800° C. for a period ranging from about 1 hour to about 20 hours. The conditions for treating the catalyst with phosphoric acid comprise, for example, treating the catalyst with a phosphoric acid solution at a concentration ranging from about 0.05 mol/l to about 15.0 mol/l at a temperature ranging from about 5° C. to about 95° C. for a period of time ranging from about 1 hour to about 20 hours, wherein the weight ratio of the phosphoric acid solution to the catalyst ranges from about 1:1 to about 20:1.

In some embodiments, the at least one binder-free ZSM-5 molecular sieve comprises at least one crystalline particle with a diameter ranging, for example, from about 10 nm to about 250 nm, such as from about 20 nm to about 200 nm. The at least one binder-free ZSM-5 molecular sieve comprises silica ($SiO_2$) and alumina ($Al_2O_3$) at a molar ratio ($SiO_2$:$Al_2O_3$) ranging, for example, from about 50:1 to about 300:1.

In some embodiments, the at least one binder-free alkylation catalyst comprises: at least one ZSM-5 molecular sieve present in an amount ranging from about 98% to about 99.9% by weight relative to the total weight of the at least one binder-free alkylation catalyst, and at least one rare earth metal oxide present in an amount ranging from about 0.1% to about 2.0% relative to the total weight of the at least one binder-free alkylation catalyst.

In some embodiments, the at least one rare earth metal oxide is chosen from lanthanum oxides, cerium oxides, and praseodymium oxides. In one embodiment, the at least one rare earth metal oxide is chosen from lanthanum oxides.

In some embodiments, the conditions for treating the at least one binder-free alkylation catalyst with steam comprise, for example, treating under atmospheric pressure and at a temperature ranging from about 480° C. to about 650° C. for a period of time ranging from about 2 hours to about 10 hours, such as from about 3 hours to about 10 hours.

In some embodiments, the conditions for treating the at least one binder-free alkylation catalyst with phosphoric acid comprise, for example, treating the catalyst with a phosphoric acid solution at a concentration of from about 0.1 mol/l to about 2.5 mol/l at a temperature in the range from about 30° C. to about 95° C. for a period of time ranging from about 2 hours to about 16 hours, such as from about 3 hours to about 16 hours, the weight ratio of the phosphoric acid solution to the catalyst ranging from about 2:1 to about 10:1.

In certain embodiments, the alkylation reaction (operation (1)) is conducted at a temperature ranging from about 320° C. to about 450° C., under a pressure ranging from about 0.5 MPa to about 2.0 MPa, at a weight hourly space velocity of ethanol ranging from about 0.6 $hour^{-1}$ to about 2.5 $hour^{-1}$, and with a molar ratio of benzene to ethanol ranging from about 4.0:1 to about 7.0:1.

In some embodiments, the benzene recovery tower is operated under a pressure ranging from about 0.4 MPaG to about 2.0 MPaG, a temperature at the top of the tower ranging from about 125° C. to about 200° C., a temperature at the bottom of the tower ranging from about 200° C. to about 300° C., and with a reflux ratio ranging from about 0.8 to about 2.

In some embodiments, the ethylbenzene recovery tower is operated under a pressure ranging from about 0.0 MPaG to about 0.5 MPaG, a temperature at the top of the tower ranging from about 135° C. to about 200° C., a temperature at the bottom of the tower ranging from about 190° C. to about 250° C., and with a reflux ratio ranging from about 2 to about 6.

In some embodiments, the polyethylbenzene recovery tower is operated under a pressure ranging from about −0.1 MPaG to about 0.2 MPaG, a temperature at the top of the tower ranging from about 100° C. to about 220° C., a temperature at the bottom of the tower ranging from about 190° C. to about 250° C., and with a reflux ratio ranging from about 0.1 to about 2.

In some embodiments, the transalkylation reaction (operation (3)) is carried out in a gas phase, the at least one transalkylation catalyst is chosen from ZSM-5 molecular sieve catalysts, and the transalkylation reactor is operated under the following conditions: a reaction temperature ranging from about 350° C. to about 460° C., a reaction pressure ranging from about 0.20 MPa to about 1.0 MPa, a total space velocity ranging from about 5 hour$^{-1}$ to about 40 hour$^{-1}$, and a weight ratio of benzene to polyethylbenzene ranging from about 3:1 to about 6:1.

In some embodiments, the transalkylation reaction (operation (3)) is carried out in a liquid phase, the transalkylation catalyst is chosen from type β and type γ molecular sieve catalysts, and the transalkylation reactor is operated under the following conditions: a reaction temperature ranging from about 150° C. to about 280° C., a reaction pressure ranging from about 2.0 MPaG to about 3.5 MPaG, a weight hourly space velocity of liquid ranging from about 1.0 hour$^{-1}$ to about 3.0 hour$^{-1}$, and a weight ratio of benzene to polyethylbenzene ranging from about 3:1 to about 6:1.

In some embodiments, the at least one binder-free alkylation catalyst is prepared by a process comprising:

i) Carrying out hydrochloric acid exchange, washing, baking, and calcinating the at least one binder-free ZSM-5 molecular sieve having a molar ratio of silica to alumina ($SiO_2/Al_2O_3$) ranging from about 30:1 to about 400:1 and at least one crystalline particle with a diameter ranging from about 5 nm to about 350 nm under conditions known to one of ordinary skill in the art, to obtain the at least one binder-free HZSM-5 molecular sieve.

ii) Loading the at least one binder-free HZSM-5 molecular sieve with at least one rare earth metallic oxide: in one embodiment, impregnating the at least one binder-free HZSM-5 molecular sieve in a rare earth saline solution at a concentration ranging from about 0.002 mol/l to about 2.0 mol/l at a temperature ranging from about 10° C. to about 60° C. for a period of time ranging from about 1 hour to about 15 hours, the weight ratio of the rare earth saline solution to the binder-free HZSM-5 molecular sieve ranging from about 0.5:1 to about 10:1; then baking, and calcinating, to obtain the binder-free HZSM-5 molecular sieve comprising the at least one rare earth oxide. In another embodiment, the rare earth saline solution is at a concentration ranging from about 0.05 mol/l to about 1.0 mol/l, the weight ratio of the rare earth saline solution to the at least one binder-free HZSM-5 molecular sieve ranges from about 1:1 to about 5:1, an impregnation temperature ranges from about 20° C. to about 40° C., and an impregnation duration ranges from about 2 hours to about 10 hours.

iii) Treating with steam: the catalyst is treated with steam at a temperature ranging from about 400° C. to about 800° C. for a period of time ranging from about 1 hour to about 20 hours so as to improve the hydrothermal stability of the catalyst.

iv) Treating with phosphoric acid: after treating the catalyst with steam, treating the catalyst with a phosphoric acid solution at a concentration ranging from about 0.05 mol/l to about 15.0 mol/l at a temperature ranging from about 5° C. to about 95° C. for a period of time ranging from about 1 hour to about 20 hours, the weight ratio of the phosphoric acid solution to the catalyst ranging from about 1:1 to about 20:1.

v) Drying and calcinating the catalyst.

In some embodiments, the at least one transalkylation catalyst comprises at least one binder. In one embodiment, the transalkylation reaction is carried out in a gas phase, and the at least one transalkylation catalyst is chosen from the ZSM-5 molecular sieve catalysts. In another embodiment, the transalkylation reaction is carried out in a liquid phase, and the at least one transalkylation catalyst is chosen from type β and type γ molecular sieve catalysts. In further another embodiment, the at least one binder-containing alkylation catalyst is used as the alkylation catalyst, and the transalkylation catalyst used thereafter can be the same or different from the at least alkylation catalyst used in the alkylation reaction. In yet another embodiment, the at least one binder-free alkylation catalyst is used as the alkylation catalyst, and the at least one transalkylation catalyst used thereafter is different from the at least one alkylation catalyst used in the alkylation reaction.

The ethanol used for the alkylation reaction may be chosen, for example, from about 95 wt. % ethanol and anhydrous ethanol.

During the alkylation reaction between benzene and ethanol in a gas phase, ethanol is dehydrated first through the action of the alkylation catalyst to generate ethylene and water; then ethylene and benzene are alkylated through the action of the same alkylation catalyst to generate ethylbenzene. Hence, a great amount of water may be produced during the alkylation reactions. However, water has a negative impact on the stability of the catalyst activity under the reaction conditions. Accordingly, treating the catalyst with a high-temperature steam may enhance hydrothermal stability of the catalyst and also improve the water-resistance of the catalyst under the reaction conditions.

Addition of at least one rare earth element to the catalyst may also help to improve hydrothermal stability and selectivity of the catalyst. For example, the at least one rare earth element may help to stabilize the aluminum framework of the molecular sieve and delay the flake-off of aluminum atoms from the framework under the high-temperature steam reaction condition, thereby maintaining the acid reactive sites of the catalyst for a long period of time.

Treating the catalyst with a phosphoric acid solution may modulate the acidic property of the molecular sieve catalyst and the distribution of Bronsted acids, Lewis Acids, and strong or weak acids to some extent, wherein the total amount of Bronsted acids may be increased, and acidity of the acids may be lowered. In addition, treatment with phosphoric acid solution may help remove amorphous substances residing within the pores of molecular sieve or the non-framework aluminum flakes that fall from the molecular sieve framework, thereby modifying the pore passages of the molecular sieve. Further, such treatment may also increase the binding force of aluminum-oxygen bonds in the molecular sieve, thereby preventing aluminum from flaking off the molecular sieve framework, improving the stability of the catalyst, and achieving the objectives of getting an extended catalyst regeneration cycle and long catalyst lifetime.

In some embodiments, ethanol and benzene are mixed together and introduced into an alkylation reactor comprising at least one ZSM-5 nanoscale molecular sieve catalyst at a high temperature, medium pressure, in a gas phase. The ethanol is then dehydrated to generate ethylene, which then reacts with benzene to generate ethylbenzene. The processes disclosed herein may have the advantages of no corrosion, no pollution, simple procedures and a high recovery rate of thermal energy. For example, ethanol is a renewable source and readily available as a starting material. Advantage of using ethanol as starting material will become increasingly evident compared to the rising price of petroleum.

In some embodiments, because the dehydration of ethanol and the alkylation of ethylene and benzene may occur simultaneously within one reactor, heat needed for the dehydration of ethanol is provided by the exothermic alkylation reaction. The ethylene generated from the ethanol dehydration and benzene are subjected to alkylation at a high temperature under a medium pressure in a gas phase, for example, at a temperature of about 400° C. and under a pressure of less than about 2.0 MPaG, and the reaction occurs in the gas phase allowing uniform mixing of the reactants.

The ZSM-5 nanoscale molecular sieve catalyst disclosed herein can allow both of the ethanol dehydration and ethylene alkylation reactions to occur simultaneously, can have high selectivity, and/or can achieve high conversion rate of ethanol to ethylene. In addition, the level of alkylation of ethylene and benzene achieved by the processes disclosure herein can be relatively similar to the level obtained with processes using ethylene instead of ethanol as a starting material.

The process disclosed herein may have a fewer side reactions, simpler procedures, lower investment, and lower operational costs as compared to a process conducting the ethanol dehydration and alkylation of ethylene and benzene separately.

In some embodiments, benzene remaining after the alkylation reaction is recycled via the benzene tower. The liquid condensation at the top of the benzene tower comprises a certain amount of water (generated from ethanol dehydration) in addition to benzene. The condenser at the top of the benzene tower may also serve as an oil-water-separation device, by which water is separated, further processed, and used as recycling water or boiler water, thus reducing the overall energy consumption of the device. A portion of the benzene after separation of water is recycled to the alkylation reactor and a portion thereof is transported into the transalkylation reactor. The water separation device can decrease the amount of water in the recycled benzene, extend the life of the catalyst, and reduce side reactions.

To increase ethylbenzene output and decrease the generation of polyethylbenzene, the present disclosure includes a transalkylation reactor wherein the transalkylation reaction is carried out between the polyethylbenzene and benzene to generate more ethylbenzene, thereby improving the overall yield of ethylbenzene.

In some embodiments, the conversion of ethanol may reach about 99.9%, the ethyl selectivity may reach about 99.0%, and the regeneration cycle of the catalyst may reach half a year under the conditions of alkylation reaction at a reaction temperature of about 390° C., under a reaction pressure of about 1.2 MPa, with a weight hourly space velocity (WHVS) of about 0.8 hour$^{-1}$ for the ethanol, and with a molar ratio of benzene to ethanol of about 6.5:1.

In some embodiments, the starting material ethanol is more than about 20% cheaper than ethylene, and the total cost of the starting materials is decreased by about 10% compared to the traditional ethylene process. The transalkylation reactor may allow more ethylbenzene to be converted from polyethylbenzene generated from the alkylation reaction, and reduces the amount of side product xylene. In one embodiment, the amount of xylene in the final product of ethylbenzene may drop from about 1,000 ppm in the traditional process to about 600 ppm in the process as disclosed herein. In another embodiment, unit consumption of ethanol is less than about 450 kg/ton ethylbenzene (calculated by 100% pure ethanol), and the energy consumption is less than about 1,000 MJ/ton ethylbenzene, and the product ethylbenzene has a purity of greater than 99.8%.

Figure 1:
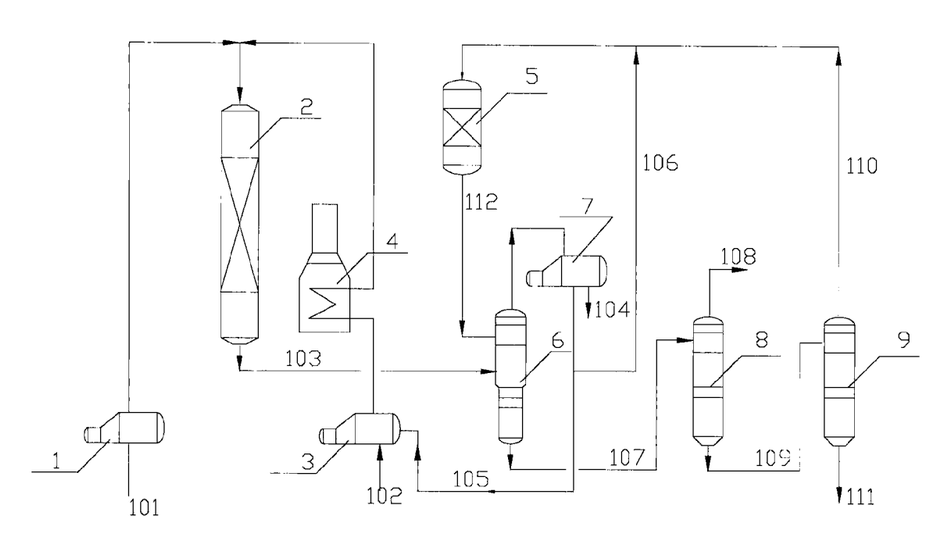
FIG. 1 represents an exemplary flow diagram for synthesizing ethylbenzene from ethanol and benzene according to the present disclosure.

In FIG. 1,
1 represents an ethanol evaporator;
2 represents an alkylation reactor;
3 represents a benzene evaporator;
4 represents a heating furnace;
5 represents a transalkylation reactor;
6 represents a benzene tower;
7 represents a condenser at the top of the benzene tower;
8 represents an ethylbenzene tower;
9 represents a polyethylbenzene tower;
101 represents a starting material ethanol;
102 represents a starting material benzene;
103 represents a stream at the outlet of the alkylation reactor;
104 represents a water stream separated from the condenser at the top of the benzene tower;
105 represents benzene, which is separated from the condenser at the top of the benzene tower and is transported to the alkylation reactor;
106 represents benzene, which is separated from the condenser at the top of the benzene tower and is transported to the transalkylation reactor;
107 represents the bottom stream of the benzene tower;
108 represents an ethylbenzene product stream at the top of the ethylbenzene tower;
109 represents a residual oil stream at the bottom of the ethylbenzene tower;
110 represents a polyethylbenzene stream at the top of the polyethylbenzene tower;
111 represents a residual oil stream at the bottom of the polyethylbenzene tower; and
112 represents a stream at the outlet of the transalkylation reactor.

In FIG. 1, the starting material ethanol 101, after being evaporated by the ethanol evaporator 1, is mixed with the mixture of the starting material benzene 102 and the recycled benzene 105, which have been heated by the benzene evaporator 3 and the heating furnace 4, and is introduced into the alkylation reactor at a high temperature under a medium pressure in gas phase for reaction, so as to generate ethylbenzene, polyethylbenzene and water. The reaction product 103 is introduced into the benzene tower 6. After the top stream of the benzene tower is condensated by the condenser 7 at the same tower top, water 104 is separated. A portion of the benzene 105 is recycled back to the alkylation reactor, and a portion of the benzene 106 is transported to the transalkylation reactor 5. The bottom stream of the benzene tower 107, which is composed mainly of ethylbenzene, polyethylbenzene, and residual oil, is transported to the ethylbenzene tower 8 and separated at the top of the tower, so as to obtain the product ethylbenzene 108. After the bottom stream 109 is separated via the polyethylbenzene tower 9, there is residual oil 111 at the bottom of the tower and polyethylbenzene 110 at the top of the tower. The polyethylbenzene 110 is mixed with the stream 106, and introduced into the transalkylation reactor 5 at a high temperature under a medium pressure in gas phase for transalkylation reaction, so as to generate more ethylbenzene products. Stream 112 at the outlet of the reactor is recycled to benzene tower 6.

The embodiments of the present disclosure described herein are representative and not limitative. Disclosed embodiments herein include the following non-limitative examples.

EXAMPLE 1

200 g of ZSM-5 molecular sieve having a molar ratio of silica to alumina ($SiO_2:Al_2O_3$) of about 100:1 and a crystalline particle size of about 200 nm was exchanged three times at 85° C. with 2 liters of 0.1 mol/l hydrochloric acid, washed with deionized water until it was free of $Cl^-$, baked at 110° C. to dry, and calcinated at 580° C. for about 4 hours before use.

20 g of said molecular sieve was impregnated with 35 ml of 0.5 mol/l lanthanum nitrate aqueous solution at room temperature for about 4 hours, then baked at 110° C. to dry, calcinated at 550° C. for about 2 hours, further mixed with alumina binder at a ratio of 70:30. Subsequently, 2% sesbania powder and 10 wt. % dilute nitrate solution were added and mixed, and the resulting mixture was extruded into a strip with a diameter ($\phi$) of 1.8 mm; baked at 110° C. for about 10 hours, then calcinated at 550° C. for about 4 hours, and a catalyst comprising 2.0 wt. % $La_2O_3$ was obtained.

The catalyst was then treated with steam under the atmospheric pressure at 580° C. for about 2 hours and with a 1.5 mol/l phosphoric acid solution at 50° C. for about 5 hours (the phosphoric acid solution and the catalyst were present at a weight ratio of 3:1), dried, and subsequently calcinated at 500° C. for about 3 hours, and the resulting catalyst was obtained.

EXAMPLES 2 TO 11

Additional catalysts were prepared according to the procedure described in the Example 1, except as shown in Table 1, different (1) molar ratio of $SiO_2/Al_2O_3$ for the ZSM-5 molecular sieve, (2) crystalline particle size, (3) ratio of the molecular sieve and alumina, (4) amount of $La_2O_3$ contained in the catalyst, and (5) conditions for steam or phosphoric treatments were used.

EXAMPLE 12

Another catalyst was prepared according to the procedure described in Example 1, with the exception that the catalyst comprised 2.0 wt. % $Ce_2O_3$.

EXAMPLE 13

Alkylation reaction between the benzene and ethanol in a gas phase for the synthesis of ethylbenzene was carried out in a continuous flowing, constant pressurized fixed bed reaction apparatus. The activity and selectivity of the catalysts according to Examples 1 to 12 were assessed. Reaction conditions: reaction temperature: 390° C.; reaction pressure: 1.2 MPa; benzene/ethanol ratio: 6.5:1 (mole/mole); and weight hourly space velocity of the ethanol: 0.8 $hour^{-1}$. See Table 1 for reaction results.

TABLE 1

| Example No. | Crystalline size nm | $SiO_2/Al_2O_3$ Molar Ratio | Molecular Sieve Weight % | Rare Earth Weight % | Steam Treatment Temperature, Time | Phosphoric acid Treatment Temperature, Time | Reaction Results Ethanol Conversion % | Ethyl Selectivity % |
|---|---|---|---|---|---|---|---|---|
| 1 | 200 | 100:1 | 70 | $La_2O_3$ 2.0 | 580° C., 2 h | 50° C., 5 h | 99.5 | 99.6 |
| 2 | 200 | 100:1 | 70 | $La_2O_3$ 1.0 | 580° C., 2 h | 50° C., 5 h | 99.6 | 99.5 |
| 3 | 200 | 100:1 | 70 | $La_2O_3$ 0.5 | 580° C., 2 h | 50° C., 5 h | 99.7 | 99.4 |
| 4 | 200 | 100:1 | 70 | $La_2O_3$ 0.1 | 580° C., 2 h | 50° C., 5 h | 99.8 | 99.3 |
| 5 | 20 | 50:1 | 65 | $La_2O_3$ 0.5 | 510° C., 3 h | 85° C., 3 h | 99.8 | 98.5 |
| 6 | 20 | 150:1 | 65 | $La_2O_3$ 0.5 | 510° C., 3 h | 85° C., 3 h | 98.7 | 99.7 |
| 7 | 20 | 200:1 | 65 | $La_2O_3$ 0.5 | 510° C., 3 h | 85° C., 3 h | 97.3 | 99.8 |
| 8 | 150 | 100:1 | 55 | $La_2O_3$ 0.5 | 480° C., 5 h | 95° C., 2 h | 99.5 | 99.5 |
| 9 | 150 | 100:1 | 60 | $La_2O_3$ 0.5 | 480° C., 5 h | 95° C., 2 h | 99.6 | 99.4 |
| 10 | 150 | 100:1 | 75 | $La_2O_3$ 0.5 | 480° C., 5 h | 95° C., 2 h | 99.7 | 99.4 |
| 11 | 150 | 100:1 | 85 | $La_2O_3$ 0.5 | 480° C., 5 h | 95° C., 2 h | 99.8 | 99.2 |
| 12 | 200 | 100:1 | 70 | $Ce_2O_3$ 2.0 | 580° C., 2 h | 50° C., 5 h | 97.2 | 97.9 |

EXAMPLE 14

The stability of the activity (i.e. the regenerating period) of the catalysts prepared according to Examples 1 to 12 was evaluated in a continuous-flowing pressurized fixed bed reaction apparatus. Reaction conditions: reaction temperature: 400° C.; reaction pressure: 1.0 MPa; benzene/ethanol ratio: 1.0:1 (mole/mole); weight hourly space velocity (WHSV) of the ethanol: 3.0 $hour^{-1}$; and reaction duration: 100 hours. See Table 2 for reaction results.

TABLE 2

| Example | Initial Ethanol Conversion, % | End Ethanol Conversion, % | Average Deactivation Rate per Hour, % |
|---------|-------------------------------|---------------------------|---------------------------------------|
| 1       | 85                            | 77                        | 0.08                                  |
| 2       | 86                            | 79                        | 0.07                                  |
| 3       | 87                            | 78                        | 0.09                                  |
| 4       | 89                            | 79                        | 0.10                                  |
| 5       | 92                            | 80                        | 0.12                                  |
| 6       | 83                            | 75                        | 0.08                                  |
| 7       | 79                            | 68                        | 0.11                                  |
| 8       | 84                            | 70                        | 0.14                                  |
| 9       | 86                            | 73                        | 0.13                                  |
| 10      | 88                            | 82                        | 0.06                                  |
| 11      | 90                            | 85                        | 0.05                                  |
| 12      | 78                            | 65                        | 0.13                                  |

EXAMPLE 15

An operating system that used ethanol and benzene to synthesize 30,000 ton/year ethylbenzene was used for this experiment. The ethylbenzene syntheses as shown in FIG. 1 were carried out as follows. Ethanol of 95% purity was heated and gasified, then mixed with gasified and heated benzene and recycled benzene. The resulting mixture was introduced into an alkylation reactor comprising ZSM-5 nano-molecular sieve catalyst, and the molar ratio of benzene to ethanol was 6:1. The inlet of the alkylation reactor was at a temperature of 380° C. under a pressure of 1.2 MPaG, and the ethanol was at a weight hourly space velocity of 1.5 hour$^{-1}$. At the end of the reaction, the material exiting the reactor was at a temperature of 400° C. and comprised 16 wt. % ethylbenzene and 1.6 wt. % diethylbenzene. The reaction product was then introduced into a benzene tower, at the top of which the operation pressure was 1.0 MPaG and the temperature was 160° C. The temperature at the bottom of the benzene tower was 250° C. The reflux ratio was 1.45:1, and float valve trays were used. After the materials from the top of the benzene tower were condensed via a condenser at the top of the benzene tower, water was separated. Benzene obtained after the water separation comprised 0.1 wt. % of water, a portion of which was recycled back to the alkylation reactor, and a portion of which was transported to a transalkylation reactor comprising ZSM-5 molecular sieve catalyst. The temperature at the inlet of said reactor was 420° C., and the pressure was 0.6 MPaG, with benzene and polyethylbenzene at a weight ratio of 5:1. The total weight hourly space velocity was 20 hour$^{-1}$, and the conversion of polyethylbenzene was 60%. The liquid at the bottom of the benzene tower was transported to a ethylbenzene tower, which was operated under a pressure of 0.1 MPaG. The temperature at the top of the ethylbenzene tower was 163° C., and the temperature at the bottom of the ethylbenzene tower was 214° C., with a reflux ratio of 3.2:1. The product ethylbenzene was obtained via the separation that occurred at top of the ethylbenzene tower. The polyethylbenzene recovery tower was operated under a pressure of −0.07 MPaG, at a temperature at the top of the tower ranging from 100° C. to 220° C. and a temperature at the bottom of the tower ranging from 190° C. to 250° C., with a reflux ratio ranging from 0.1:1 to 2:1. The liquid condensed at the top of the tower was polyethylbenzene and was further transported to the transalkylation reactor. The stream obtained at the bottom of the tower was residual oil.

The total cost of the starting materials used in the operating system was 8,950 RMB per ton of ethylbenzene with 99.82% purity. Unit consumption of ethanol was 440 kg per ton of ethylbenzene. Energy consumption was 960 MJ per ton of ethylbenzene.

EXAMPLE 16

An operating system that used ethanol and benzene to synthesize 30,000 ton/year ethylbenzene was used for this experiment. The molar ratio of benzene to ethanol was 5:1 in the alkylation reactor. The other processing procedures and operation parameters were the same as those described in Example 15. There were 15 wt. % of ethylbenzene and 2.0 wt. % of diethylbenzene in the materials exiting the alkylation reactor.

The total cost of starting materials used in the operating system was 9,010 RMB per ton of ethylbenzene with 99.8% purity. Unit consumption of ethanol was 446 kg per ton of ethylbenzene. Energy consumption was 920 MJ per ton of ethylbenzene.

EXAMPLE 17

An operating system that used ethanol and benzene to synthesize 60,000 ton/year ethylbenzene was used for this experiment. The temperature at the inlet of the alkylation reactor was 400° C. The other processing procedures and operation parameters were the same as those described in Example 15. There were 16 wt. % of ethylbenzene and 1.65 wt. % of diethylbenzene in the materials exiting the alkylation reactor.

The total cost of starting materials used in the operating system was 8,990 RMB per ton of ethylbenzene with 99.82% purity. Unit consumption of ethanol was 442 kg per ton of ethylbenzene. Energy consumption was 980 MJ per ton of ethylbenzene.

EXAMPLE 18

An operating system that used ethanol and benzene to synthesize 60,000 ton/year ethylbenzene was used for this experiment. The temperature at the inlet of the transalkylation reactor was 440° C. The weight ratio of benzene and polyethylbenzene was 6:1. A total weight hourly space velocity was 20 hour$^{-1}$. The conversion of polyethylbenzene was 50%. The other processing procedures and operation parameters were the same as those described in Example 15.

The total cost of starting materials used in said apparatus was 8,930 RMB per ton of ethylbenzene with 99.78% purity. Unit consumption of ethanol was 439 kg per ton of ethylbenzene. Energy consumption was 970 MJ per ton of ethylbenzene.

EXAMPLE 19

50 g of a binder-free ZSM-5 molecular sieve catalyst having a silica to alumina ($SiO_2/Al_2O_3$) molar ratio of 200:1, a crystalline particle size of 150 nm, and a particle diameter of a diameter ($\phi$) of 1.8 mm was exchanged three times with 0.5 liter of 0.1 mol/l hydrochloric acid at 85° C., washed with deionized water until it is free of Cl$^-$, baked at 110° C. to dry, and calcinated at 580° C. for 4 hours before use.

20 g of said catalyst was impregnated with 40 ml of 0.4 mol/l lanthanum nitrate aqueous solution at room temperature for 4 hours, then baked at 110° C. to dry for 10 hours, and later calcinated at 550° C. for 4 hours so as to obtain a catalyst comprising 2.0 wt. % $La_2O_3$.

The catalyst was treated with steam under the atmospheric pressure at 580° C. for 3 hours, then treated with a 1.5 mol/l phosphoric acid solution at 50° C. for 5 hours (the weight ratio of the phosphoric acid solution and the catalyst was 3:1), dried, and subsequently calcinated at 500° C. for 3 hours so as to obtain the resulting catalyst.

EXAMPLES 20 TO 28

The catalysts were prepared according to the procedure described in the Example 19, except as shown in Table 3, different (1) molar ratio of $SiO_2/Al_2O_3$, (2) crystalline particle size, (3) amount of $La_2O_3$ in the catalyst, (4) conditions for the treatment with steam and phosphoric acid were used.

EXAMPLE 29

The catalyst was prepared according to the procedure described in the Example 19, with the exception that the catalyst comprised 2.0 wt. % $Ce_2O_3$.

EXAMPLE 30

Alkylation between benzene and ethanol in gas phase for production of ethylbenzene was carried out in a continuous-flowing, constant pressurized fixed bed reaction system. The activity and selectivity of the catalysts prepared according to Examples 19 to 29 were evaluated. Reaction conditions: reaction temperature: 390° C.; reaction pressure: 1.2 MPa: benzene/ethanol ratio: 6.5:1 (mole/mole); and weight hourly space velocity of the ethanol: 0.8 hour$^{-1}$. See Table 3 for reaction results.

TABLE 3

| Example No. | Crystalline size nm | $SiO_2/Al_2O_3$ Molar Ratio | Rare Earth Weight % | Steam Treatment Temperature, Time | Phosphoric Treatment Temperature, Time | Reaction Results | |
|---|---|---|---|---|---|---|---|
| | | | | | | Ethanol Conversion % | Ethyl Selectivity % |
| 19 | 150 | 200:1 | $La_2O_3$ 2.0 | 580° C., 3 h | 50° C., 5 h | 99.7 | 99.8 |
| 20 | 150 | 200:1 | $La_2O_3$ 1.0 | 580° C., 3 h | 50° C., 5 h | 99.8 | 99.7 |
| 21 | 150 | 200:1 | $La_2O_3$ 0.5 | 580° C., 3 h | 50° C., 5 h | 100.0 | 99.6 |
| 22 | 150 | 200:1 | $La_2O_3$ 0.1 | 580° C., 3 h | 50° C., 5 h | 100.0 | 99.5 |
| 23 | 150 | 50:1 | $La_2O_3$ 0.5 | 510° C., 4 h | 85° C., 3 h | 100.0 | 99.5 |
| 24 | 150 | 150:1 | $La_2O_3$ 0.5 | 510° C., 4 h | 85° C., 3 h | 100.0 | 99.7 |
| 25 | 150 | 300:1 | $La_2O_3$ 0.5 | 510° C., 4 h | 85° C., 3 h | 99.2 | 99.8 |
| 26 | 20 | 100:1 | $La_2O_3$ 0.5 | 480° C., 6 h | 95° C., 2 h | 100.0 | 99.3 |
| 27 | 100 | 100:1 | $La_2O_3$ 0.5 | 480° C., 6 h | 95° C., 2 h | 100.0 | 99.5 |
| 28 | 200 | 100:1 | $La_2O_3$ 0.5 | 480° C., 6 h | 95° C., 2 h | 100.0 | 99.6 |
| 29 | 150 | 200:1 | $Ce_2O_3$ 2.0 | 580° C., 3 h | 50° C., 5 h | 99.1 | 98.5 |

EXAMPLE 31

In a continuous-flowing pressurized fixed bed reaction system, the stability of the activity (i.e., the period of the regeneration cycle) of the catalysts prepared according to Examples 19 to 29 was evaluated. Reaction conditions: reaction temperature: 400° C.; reaction pressure: 1.0 MPa; benzene/ethanol ratio: 1.0:1 (mole/mole); weight hourly space velocity (WHSV) of ethanol: 3.0 hour$^{-1}$; and reaction duration: 100 hours. See Table 4 for reaction results.

TABLE 4

| Example | Initial Ethanol Conversion, % | End Ethanol Conversion, % | Average Deactivation Rate per Hour, % |
|---|---|---|---|
| 19 | 89 | 84 | 0.05 |
| 20 | 90 | 87 | 0.03 |
| 21 | 91 | 86 | 0.05 |
| 22 | 92 | 84 | 0.08 |
| 23 | 95 | 87 | 0.08 |
| 24 | 92 | 86 | 0.06 |
| 25 | 89 | 84 | 0.05 |
| 26 | 96 | 87 | 0.09 |
| 27 | 93 | 85 | 0.07 |
| 28 | 91 | 86 | 0.05 |
| 29 | 90 | 79 | 0.11 |

What is claimed is:

1. A process for synthesizing ethylbenzene from ethanol and benzene, comprising:
   1) reacting a first mixture comprising ethanol and benzene at a molar ratio ranging from about 2:1 to about 8:1 with at least one binder-containing alkylation catalyst in an alkylation reactor to obtain a second mixture comprising benzene, ethylbenzene, diethylbenzene, and water;
   2) passing the second mixture successively through a benzene recovery tower, an ethylbenzene recovery tower, and a polyethylbenzene recovery tower to obtain separated water, separated benzene, separated ethylbenzene, and separated diethylbenzene; and
   3) reacting a third mixture with at least one transalkylation catalyst in a transalkylation reactor, wherein the third mixture comprises at least some of the separated benzene and at least some of the separated diethylbenzene at a weight ratio ranging from about 2:1 to about 10:1,
   wherein the at least one binder-containing alkylation catalyst comprises:
   a) at least one ZSM-5 molecular sieve present in an amount ranging from about 40% to about 90% by weight relative to the total weight of the at least one binder-containing alkylation catalyst, wherein the at least one ZSM-5 molecular sieve comprises:

silica (SiO$_2$) and alumina (Al$_2$O$_3$) at a molar ratio (SiO$_2$:Al$_2$O$_3$) ranging from about 30:1 to about 400:1, and at least one crystalline particle with a diameter ranging from about 5 nm to about 350 nm;
  b) at least one rare earth metal oxide present in an amount ranging from about 0.1% to about 10% by weight relative to the total weight of the at least one binder-containing alkylation catalyst; and
  c) at least one binder chosen from alumina and silica present in an amount ranging from about 9% to about 59% by weight relative to the total weight of the at least one binder-containing alkylation catalyst;
  wherein the at least one binder-containing alkylation catalyst has been treated:
  (i) with steam under atmospheric pressure and at a temperature ranging from about 400° C. to about 800° C. for a period of time ranging from about 1 hour to about 20 hours; and
  (ii) with a phosphoric acid solution at a concentration ranging from about 0.05 mol/l to about 15.0 mol/l and at a temperature ranging from about 5° C. to about 95° C. for a period of time ranging from about 1 hour to about 20 hours, and wherein the weight ratio of the phosphoric acid solution to the at least one binder-containing catalyst ranges from about 1:1 to about 20:1.

2. The process according to claim 1, wherein the at least one ZSM-5 molecular sieve comprises at least one crystalline particle with a diameter ranging from about 20 nm to about 200 nm.

3. The process according to claim 1, wherein the silica (SiO$_2$) and the alumina (Al$_2$O$_3$) is present at a molar ratio (SiO$_2$:Al$_2$O$_3$) ranging from about 50:1 to about 300:1 in the at least one ZSM-5 molecular sieve.

4. The process according to claim 1, wherein the at least one binder-containing alkylation catalyst comprises:
  the at least one ZSM-5 molecular sieve in an amount ranging from about 55% to about 85% by weight relative to the total weight of the at least one binder-containing alkylation catalyst,
  the at least one binder in an amount ranging from about 14% to about 44% by weight relative to the total weight of the at least one binder-containing alkylation catalyst, and
  the at least one rare earth metal oxide in an amount ranging from about 0.1% to about 2.0% by weight relative to the total weight of the at least one binder-containing alkylation catalyst.

5. The process according to claim 1, wherein the at least one rare earth metal oxide is chosen from lanthanum oxides, cerium oxides, and praseodymium oxides.

6. The process according to claim 5, wherein the at least one rare earth metal oxide is chosen from lanthanum oxides.

7. The process according to claim 1, wherein the at least one binder-containing catalyst has been treated:
  with the steam under atmospheric pressure and at a temperature ranging from about 480° C. to about 650° C. for a period of time ranging from about 2 hours to about 10 hours; and
  with the phosphoric acid solution at a concentration of about 0.1 ma/l to about 2.5 mol/l and at a temperature ranging from about 30° C. to about 95° C. for about 2 hours to about 16 hours, the weight ratio of the phosphoric acid solution to the at least one binder-containing catalyst ranging from about 2:1 to about 10:1.

8. The process according to claim 1, wherein the reaction in the alkylation reactor is conducted at a temperature ranging from about 320° C. to about 450° C. and under a pressure ranging from about 0.5 MPa to about 2.0 MPa, at a weight hourly space velocity of the ethanol ranging from about 0.6 to about 2.5 hour$^{-1}$, and with a molar ratio of the benzene to the ethanol ranging from about 4.0:1 to about 7.0:1.

9. The process according to claim 1, wherein the benzene recovery tower is operated:
  under a pressure ranging from about 0.4 MPaG to about 2.0 MPaG, a temperature at the top of the tower ranging from about 125° C. to about 200° C., a temperature at the bottom of the tower ranging from about 200° C. to about 300° C., and with a reflux ratio ranging from about 0.8:1 to about 2:1.

10. The process according to claim 1, wherein the ethylbenzene recovery tower is operated:
  under a pressure ranging from about 0.0 MPaG to about 0.5 MPaG, a temperature at the top of the tower ranging from about 135° C. to about 200° C., a temperature at the bottom of the tower ranging from about 190° C. to about 250° C., and with a reflux ratio ranging from about 2:1 to about 6:1.

11. The process according to claim 1, wherein the polyethylbenzene recovery tower is operated:
  under a pressure ranging from about −0.1 MPaG to about 0.2 MPaG, a temperature at the top of the tower ranging from about 100° C. to about 220° C., a temperature at the bottom of the tower ranging from about 190° C. to about 250° C., and with a reflux ratio is from about 0.1:1 to about 2:1.

12. The process according to claim 1, wherein the reaction in the transalkylation reactor is carried out in a gas phase, the at least one transalkylation catalyst is chosen from ZSM-5 molecular sieve catalysts, and the transalkylation reactor is operated under conditions comprising:
  a temperature ranging from about 350° C. to about 460° C.,
  a pressure ranging from about 0.20 to about 1.0 MPa,
  a total space velocity ranging from about 5 hour$^{-1}$ to about 40 hour$^{-1}$, and
  a weight ratio of benzene to polyethylbenzene ranging from about 3:1 to about 6:1.

13. The process according to claim 1, wherein the reaction in the transalkylation reactor is carried out in a liquid phase, the at least one transalkylation catalyst is chosen from type β and type γ molecular sieve catalysts, and the transalkylation reactor is operated under conditions comprising:
  a temperature ranging from about 150° C. to about 280° C.,
  a pressure ranging from about 2.0 MPaG to about 3.5 MPaG,
  a weight hourly space velocity of liquid ranging from about 1.0 hour$^{-1}$ to about 3.0 hour$^{-1}$, and
  a weight ratio of benzene to polyethylbenzene ranging from about 3:1 to about 6:1.

14. A process for synthesizing ethylbenzene from ethanol and benzene, comprising:
  1) reacting a first mixture comprising ethanol and benzene at a molar ratio ranging from about 2:1 to about 8:1 with at least one binder-free alkylation catalyst in an alkylation reactor to produce a second mixture comprising benzene, ethylbenzene, diethylbenzene, and water;
  2) passing the second mixture successively through a benzene recovery tower, an ethylbenzene recovery tower, and a polyethylbenzene recovery tower to obtain separated water, separated benzene, separated ethylbenzene, and separated diethylbenzene;
  3) reacting a third mixture with at least one transalkylation catalyst in a transalkylation reactor, wherein the third mixture comprises at least some of the separated benzene and at least some of the separated diethylbenzene at a weight ratio ranging from about 2:1 to about 10:1, wherein the at least one binder-free alkylation catalyst comprises:
a) at least one binder-free ZSM-5 molecular sieve present in an amount ranging from about 90% to about 99.9% by weight relative to the total weight of the at least one binder-free alkylation catalyst, wherein the at least one ZSM-5 molecular sieve comprises silica ($SiO_2$) and alumina ($Al_2O_3$) at a molar ratio ($SiO_2$:$Al_2O_3$) ranging about 30:1 to about 400:1 and at least one crystalline particle with a diameter ranging from about 5 nm to about 350 nm; and
b) at least one rare earth metal oxide present in an amount ranging from about 0.1% to about 10% by weight relative to the total weight of the at least one binder-free alkylation catalyst;

wherein the at least one binder-free alkylation catalyst has been treated:
(i) with steam under atmospheric pressure at a temperature ranging from about 400° C. to about 800° C. for a period of time ranging from about 1 hour to about 20 hours; and
(ii) with a phosphoric acid solution at a concentration ranging from about 0.05 mol/l to about 15.0 mol/l and at a temperature ranging from about 5° C. to about 95° C. for a period of time ranging from about 1 hour to about 20 hours, and wherein the weight ratio of the phosphoric acid solution to the at least one binder-free catalyst ranges from about 1:1 to about 20:1.

15. The process according to claim 14, wherein the at least one ZSM-5 molecular sieve comprises crystalline particles with diameter ranging from about 20 nm to about 200 nm.

16. The process according to claim 14, wherein the silica ($SiO_2$) and the alumina ($Al_2O_3$) is present at a molar ratio ($SiO_2$:$Al_2O_3$) ranging from about 50:1 to about 300:1 in the at least one ZSM-5 molecular sieve.

17. The process according to claim 14, wherein the at least one binder-free alkylation catalyst comprises:
the at least one binder-free ZSM-5 molecular sieve in an amount ranging from about 98% to about 99.9% by weight relative to the total weight of the at least one binder-free alkylation catalyst, and
the at least one rare earth metal oxide in an amount ranging from about 0.1% to about 2.0% by weight relative to the total weight of the at least one binder-free alkylation catalyst.

18. The process according to claim 14, wherein the at least one rare earth metal oxide is chosen from lanthanum oxides, cerium oxides, and praseodymium oxides.

19. The process according to claim 18, wherein the at least one rare earth metal oxide is chosen from lanthanum oxides.

20. The process according to claim 19, wherein the at least one binder-free catalyst has been treated:
with the steam under atmospheric pressure and at a temperature ranging from about 480° C. to about 650° C. for a period of time ranging from about 2 hours to about 10 hours; and
with the phosphoric acid solution at a concentration of about 0.1 mol/l to about 2.5 mol/l and at a temperature ranging from about 30° C. to about 95° C. for a period of time ranging from about 2 hours to about 16 hours, the weight ratio of the phosphoric acid solution to the at least one binder-containing catalyst ranging from about 2:1 to about 10:1.

21. The process according to claim 14, wherein the reaction in the alkylation reactor is conducted at a temperature ranging from about 320° C. to about 450° C. and under a pressure ranging from about 0.5 MPa to about 2.0 MPa, at a weight hourly space velocity of the ethanol ranging from about 0.6 to about 2.5 hour$^{-1}$, and with a molar ratio of the benzene to the ethanol ranging from about 4.0:1 to about 7.0:1.

22. The process according to claim 14, wherein the benzene recovery tower is operated:
under a pressure ranging from about 0.4 MPaG to about 2.0 MPaG, a temperature at the top of the tower ranging from about 125° C. to about 200° C., a temperature at the bottom of the tower ranging from about 200° C. to about 300° C., and with a reflux ratio ranging from about 0.8:1 to about 2:1.

23. The process according to claim 14, wherein the ethylbenzene recovery tower is operated:
under a pressure ranging from about 0.0 MPaG to about 0.5 MPaG, a temperature at the top of the tower ranging from about 135° C. to about 200° C., a temperature at the bottom of the tower ranging from about 190° C. to about 250° C., and with a reflux ratio ranging from about 2:1 to about 6:1.

24. The process according to claim 14, wherein the polyethylbenzene recovery tower is operated:
under a pressure ranging from about −0.1 MPaG to about 0.2 MPaG, a temperature at the top of the tower ranging from about 100° C. to about 220° C., a temperature at the bottom of the tower ranging from about 190° C. to about 250° C., and with a reflux ratio ranging from about 0.1:1 to about 2:1.

25. The process according to claim 14, wherein the reaction in the transalkylation reactor is carried out in a gas phase, the at least one transalkylation catalyst is chosen from ZSM-5 molecular sieve catalysts, and the transalkylation reactor is operated under the conditions comprising:
a temperature ranging from about 350° C. to about 460° C.,
a pressure ranging from about 0.20 to about 1.0 MPa,
a total space velocity ranging from about 5 hour$^{-1}$ to about 40 hour$^{-1}$, and
a weight ratio of benzene to polyethylbenzene ranging from about 3:1 to about 6:1.

26. The process according to claim 14, wherein the reaction in the transalkylation reactor is carried out in a liquid phase, the at least one transalkylation catalyst is chosen from type β and type γ molecular sieve catalysts, and the transalkylation reactor is operated under the conditions comprising:
a temperature ranging from about 150° C. to about 280° C.,
a pressure ranging from about 2.0 MPaG to about 3.5 MPaG,
a weight hourly space velocity of liquid ranging from about 1.0 hour$^{-1}$ to about 3.0 hour$^{-1}$, and
a weight ratio of benzene to polyethylbenzene ranging from about 3:1 to about 6:1.

* * * * *

UNITED STATES PATENT AND TRADEMARK OFFICE
CERTIFICATE OF CORRECTION

PATENT NO.      : 8,519,208 B2
APPLICATION NO. : 13/158709
DATED           : August 27, 2013
INVENTOR(S)     : Weimin Yang et al.

Page 1 of 1

It is certified that error appears in the above-identified patent and that said Letters Patent is hereby corrected as shown below:

Title Page, item 73, line 4, "Shangai" should read -- Shanghai --.

Signed and Sealed this
Twenty-eighth Day of January, 2014

Michelle K. Lee
*Deputy Director of the United States Patent and Trademark Office*